Figure 1:
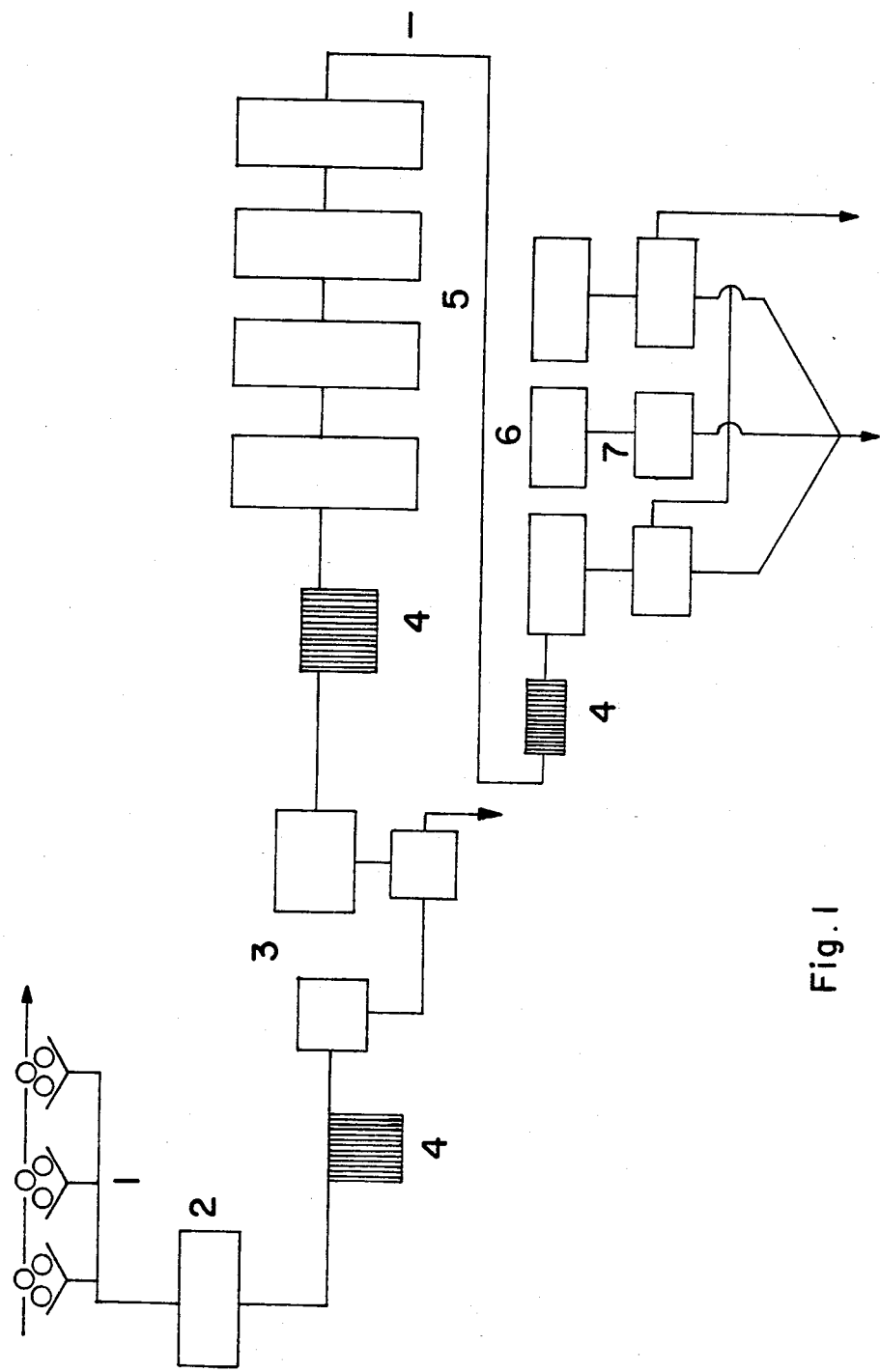

__United States Patent__ [19]

Pellegrini

[11] Patent Number: 4,544,558

[45] Date of Patent: Oct. 1, 1985

[54] PROCESS FOR PREPARING CARBOHYDRATES FROM VEGETAL JUICE

[76] Inventor: Armando P. Pellegrini, Rua General Dionisio Cerqueira, 307, 30.000 Belo Horizonte, Minas Gerais, Brazil

[21] Appl. No.: 497,056

[22] Filed: May 23, 1983

Related U.S. Application Data

[63] Continuation-in-part of Ser. No. 375,277, filed as PCT BR 81/00005, Aug. 13, 1981, published as WO 82/00662, Mar. 4, 1982, § 102(e) date Apr. 26, 1982, abandoned.

[30] Foreign Application Priority Data

Aug. 27, 1980 [BR] Brazil ............................. PI 8005458

[51] Int. Cl.$^4$ ......................... C13K 1/06; C13K 1/10; C12P 19/24; C12P 19/20; C12P 19/14; C12P 7/06; C12P 7/08; C12P 7/14

[52] U.S. Cl. ....................................... 426/48; 426/51; 426/52; 435/94; 435/95; 435/96; 435/99; 435/161; 435/162

[58] Field of Search ............ 435/94, 96, 98, 99, 435/161–163, 165, 255, 274, 276; 426/51–53, 60; 127/58; 426/48

[56] References Cited

U.S. PATENT DOCUMENTS 3,897,305  7/1975  Hurst ..................................... 435/96
3,990,944  11/1976  Gauss et al. ......................... 435/165
3,992,260  11/1976  Suzuki et al. ....................... 435/99 X
4,009,075  2/1977  Hoge ................................... 340/347 AD
4,111,750  9/1978  Colilla et al. ......................... 435/179

Primary Examiner—Lionel M. Shapiro
Attorney, Agent, or Firm—Cushman, Darby & Cushman

[57] ABSTRACT

A process for producing carbohydrates from vegetal juice comprises extracting a vegetal juice from raw vegetal material, filtering the vegetal juice to remove material suspended therein, subjecting the resultant vegetal juice to an enzymatic reaction which consists of four stages in the following sequence. The vegetal juice in a first stage is admixed with a mixture of 3.2.1.4-$\beta$-1,4-glucan glucanhydrolase and 3.2.1.15-poly-$\alpha$-1,4-galacturonic glucanhydrolase, then the vegetal juice is admixed with 3.2.1.20-$\alpha$-D-glucoside glucohydrolase. In the second stage the vegetal juice is admixed with 3.2.1.20-$\alpha$-D-glucoside glucohydrolase; in the third state the vegetal juice is contacted with 3.2.1.21-$\beta$-D-glucoside glucohydrolase, 5.3.1.4-L-arabinose-ketol-isomerase and 5.3.1.5-D-xylose-ketol-isomerase; and in the fourth stage the vegetal juice is admixed with 3.2.1.1-$\alpha$-1,4-glucan-4-glucanhydrolase.

Thereafter the enzymatic treated juice is filtered, evaporated under reduced pressure to remove water and crystallized to produce said carbohydrates in a single solid form.

5 Claims, 2 Drawing Figures

PROCESS FOR PREPARING CARBOHYDRATES FROM VEGETAL JUICE

This application is a continuation-in-part of our application, Ser. No. 375,277 filed as PCT BR 81/0005, Aug. 13, 1981, published as WO 82/00662, Mar. 4, 1982, § 102(e) date Apr. 26, 1982, now abandoned the disclosure of which is incorporated herein by reference.

The present invention refers to an enzymatic process for producing carbohydrates derived from vegetal juice.

In so far as the process for the production of carbohydrates from vegetal juice is concerned, no substantial modification has been introduced in recent years, except for some mechanical improvements in devices used for their production. Thus, the process continues to be based on the crystallization of sucrose and the simple separation of the resulting solid phase from the liquid phase.

In its essential form, the utilization of carbohydrates is wide spread throughout the world. On fermentation of carbohydrates, alcohol is produced which would suffice to justify their importance. In the area of esterification, biodegradable detergents are produced whose non-polluting significance need not be elaborated, these detergents representing a large field of use.

On acid degradation of carbohydrates in addition to other compounds, furfural is produced; on alkalization, lactic acid is produced having a wide range of uses including food, esters, plasticizers and plastics. On oxidation, allylation and a wide spectrum of hydrogenation reactions of carbohydrates, including numerous secondary reactions, food, resins, plastics, plasticizers, explosives, cosmetics, adhesives, and the like, are produced.

Currently, large scale production of carbohydrates from sugar cane, beets, sorghum or any syrup capable of producing crystalline carbohydrates, proceeds according to the following overall scheme: initially, the raw material is introduced into machines that mechanically remove the juice. Thereafter, the impurities are precipitated by chemical and thermic operations, after which the impurities are removed by conventional filtration procedures, the filtrate then being subjected to vacuum concentrator and crystallization operations ending with the separation of the resulting solid and liquid phases.

Practically, all the production of carbohydrates, the condensation ones of high molecular weight, and those of three, five and six carbons, leads to the production of the best utilized soluble form, i.e. the α-delta-glucopyranosis.

It is known that the types of carbohydrates most common in nature are celluloses and starch, the latter as reserve nourishment for plants and the former constituting their skeleton, both of which are insoluble in water. With the exception of these two, the carbohydrates occurring in nature form solutions, a portion of which can be transformed into solid matter and a portion, not withstanding technological progresses which remains liquid, often even in quantitatively high levels.

From an industrial viewpoint, the existence of the two phases is disadvantageous because, in addition to the depletion of the solid phase, the liquid phase is subject to chemical and biological reactions which generally are not controllable.

The process of the present invention thus relates to the production of carbohydrates comprising the implementation of specific controlled enzymatic reactions on previously determined substrates, of the juice, without reacting with the remaining components thereby producing, in the end, the solid phase only. With this process of invention, by the judicious utilization of adequate hydrolases and of transferases of the enzymes classification, it is possible to obtain completely crystallizable and soluble carbohydrates that can be stored over long time periods without decomposition, these carbohydrates being capable of being subjected to reactions such as hydrogenation, esterification, oxidation and the like.

In the process of the present invention the utilization of enzymes reacting in successive steps, provides the total transformation of carbohydrates in carbohydrates of six to twelve carbons, for direct use or for further development, arising from a primary product exclusively in the solid phase. In this process, the action of hydrolases-oxireductases-transferases, on the juice only, results in specific and final sectors that sometimes even nature does not manage to attain.

For a better understanding, the carbohydrate product of the conventional process, and the carbohydrates obtained by the process of the present invention are defined in qualitative terms:

| Conventional Process | | Enzymatic Process (Present Invention) | |
|---|---|---|---|
| Sucrose → (Solid) | | Sucrose | } Main Carbohydrates (Solids) (Solids) |
| Glucose | } Main Carbohydrates (Liquid) | Glucose | |
| Fructose | | | |
| Galactose | } Secondary Carbohydrates (Liquid) | Uronic Acid | } Secondary Carbohydrates (Solids) |
| Xylose | | | |
| Ramnose | | Methoxyl | |
| Arabinose | | | |
| Pectins | | | |
| Starch | | | |
| Uronic Acid | | | |
| Methoxyl | | | |
| Gums | | | |
| Colloids | | | |
| Aconitic Acid | } Other Carbohydrates (Liquid) | Aconitic Acid | } Other Carbohydrates (Solid) |
| Inosite | | Inosite | |
| Phytin | | Phytin | |
| Basic Ashes | } Liquid | Basic Ashes | } Solids |
| Acid Ashes | | Acid Ashes | |
| Proteins | | Proteins | |
| Aminoacids | | Aminoacids | |
| Esteroids and Waxes | } Liquid | Esteroids and Waxes | } Solid |
| Antocyanins | } Pigments (Liquid) | Pigments (Traces) | } Solid |
| Chlorophyll | | | |
| Polyphenols | | | |
| Tannin | | | |
| Vitamins | } Liquid | Vitamins | } Solid |
| B Complex | | B Complex | |

From a comparison of both types of products, it is clear that the product of the enzymatic process presents extremely important aspects. Because of the initial treatment of the juice, the resulting carbohydrates when incorporated into a final product enhance the latter's nourishment characteristics because of the carbohydrates' greater nutritive value, since the carbohydrates such as gums, colloids, xylose, arabinoses, starch, dextrines, pectins, ramnose and galactose, are transformed into glucose. Moreover the carbohydrates produced in accordance with the present invention are important in the production of industrial alcohol, since the carbohydrates have 90–92% of TRS, and all of these are fermentable thereby, yielding, under well controlled conditions, up to 90% output in the production of ethanol, and in the stillage only 0.19% of non-fermentables, rather than 3–8% which is the usual case.

The carbohydrates of the present invention are defined as being those produced by an enzymatic process wherein the end product is composed of a single solid phase. By acting on the extract under controlled conditions, the direction of the reaction dynamics are so induced as to be capable of completing nature's actions. By acting on previously determined substrates the present invention produces a specific and defined product that basically maintains all the initial components, since only reactions that were interrupted in the so called "relative vegetal cycle" are completed, of which the juice is its natural and primary vehicle.

For a better comprehension of the invention, reference is made to the drawings which are flow charts of both the conventional process and enzymatic process of the present invention.

Figure 2:
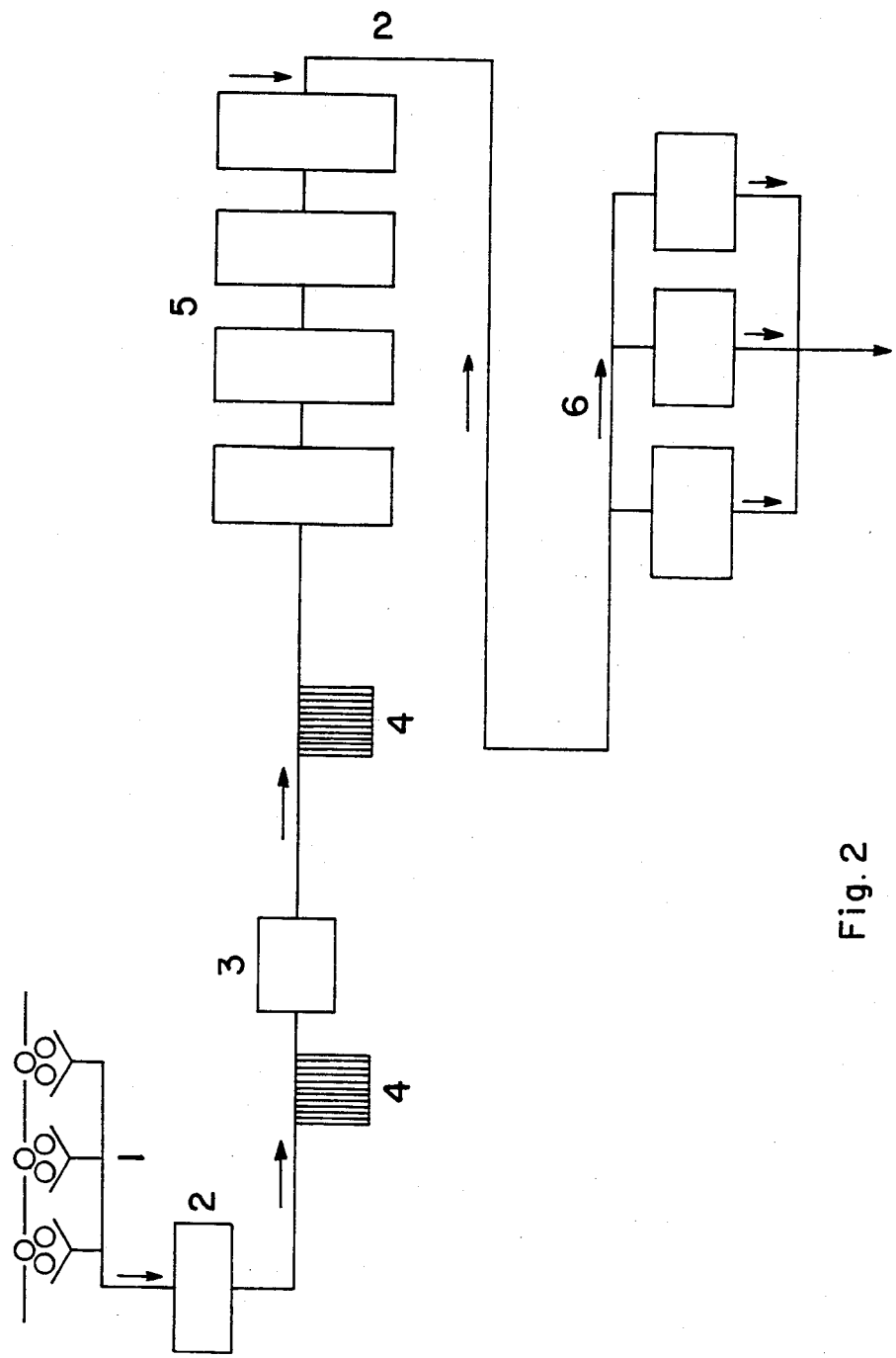

FIG. 1 shows a simplified flow chart of the basic steps of a currently used industrial process, and FIG. 2 shows a simplified flow chart of the basic steps of the process, according to the present invention.

In FIG. 1, the juice is extracted from the vegetal matter by a conventional expeller (1) and introduced into filter means (2) which can be provided with a wire grid so as to remove gross material in suspension in the extracted juice. The juice is then heated by heater means (3) where the juice is cleaned by heat, chemical coagulation and even ionic exchange. Plate heaters (4) are provided to increase the temperature of the extracted juice. A series of vacuum concentrator batteries (5) are provided where most of the water is eliminated after which the material is passed to solidifiers (6) and then to centrifugal separators (7), where solids are finally separated.

FIG. 2 shows the process of the present invention wherein some of the heaters (3), the centrifugal separators (7) and some plate heaters (4) are excluded, whereas other conventional components already cited remain and wherein enzymatic reaction unit (8) is added.

The process of the present invention is carried out in the following manner. By means of the diffuser or extractor (1), the extract juice is obtained from the vegetal material, the extracted juice containing carbohydrates dissolved therein. There is no need to control the pH, since the vegetal extracts are in the 3.5–8 range where the proposed enzymes act, and the reaction times in the unit (8), vary from 20 to 90 min. The temperature should remain between 18°–67° C. The enzymes utilized in enzyme reactor (8) are listed below, by the number corresponding to their international classification, and in the present case they vary from 3.2.1.1 (4-glucan-4-glucanhydrolase) to 5.3.1.5 (D-xylose-ketol-isomerase), in the following reactions:

| Name | Dosage (Quantity) |
|---|---|
| 1st stage with addition: | |
| 3.2.1.4-β-1,4-glucan glucanhydrolase | 1.5 U |
| 3.2.1.15-Poly-α-1,4-galacturonic glucanhydrolase | 0.9 U |
| 2nd stage with addition: | |
| 3.2.1.20-α-D-glucoside glucohydrolase | 0.3 U |
| 3rd stage with addition: | |
| 3.2.1.21-β-D-glucoside glucohydrolase | 0.3 U |
| 5.3.1.4-L-arabinose-ketol-isomerase | 0.15 U |
| 5.3.1.5-D-xylose-ketol-isomerase | 0.15 U |
| 4th stage with addition: | |
| 3.2.1.1-α-1,4-glucan-4-glucanhydrolase | 0.12 U |
| 3.2.1.3-α-1,4-glucan glucanhydrolase | 0.22 U |

The enzymatic temperature and reaction time for each of the four stages of the overall enzymatic reaction in reactor (8) are as follows:

| 1st stage | 62° C. during 20 minutes |
| 2nd stage | 65° C. during 30 minutes |
| 3rd stage | 65° C. during 20 minutes |
| 4th stage | 68° C. during 20 minutes |

The dosage "U" of the enzymes corresponds to the amount necessary for the treatment of 1,000 liters of juice under normal conditions and is equivalent to the amount capable of hydrolyzing in 10 min. one mol of starch.

After the enzymatic reaction stage is completed, the temperature of the thus extracted material is raised to 90°–100° C. by means of heaters (3) so as to clot all impurities that remain, as well as the albuminoids, and to inactivate the enzymes. The material is then passed to filtration or centrifugation means so as to obtain a clean juice measuring 13°–17° Brix. The juice is then sent to vacuum concentrators (5) to eliminate practically all water, the concentrators being maintained at a temperature not above 70° C. and yielding a juice measuring about 70° Brix. Once adequate saturation is reached so that the juice forms crystals, the product is mixed at low speed in the crystallizers (6) until the granules separate by themselves.

The end product must have a relative humidity of less than 0.5%, preferably 0.25%. The resulting concentrate is composed of carbohydrates with no liquid phase being present. The process of the present invention, provides, as an option, that the concentrate is sent to a "spray-dryer" or Turbo-dryer to form an even powder or granulate which can be used directly or in further industrial operations of the types mentioned previously.

Some of the more significant advantages achieved using the process of the present invention include
 no losses in the primary process;
 a single solid phase in the resulting primary product;
 a strictly natural product composition;
 an absence of effluents and by-products;
 about 30% higher end production;
 greater storage and transportation facility;
 lower production cost because of the low enzyme quantities employed;
 elimination of part of the conventional equipment currently used;
 a simplified process with consequent industrial costs reduction; and,
 an integral solid phase of natural components, without depletion due to phase partition.

The following is a comparative plan of the conventional process and the enzymatic process of the present invention.

| Conventional | Enzymatic |
| --- | --- |
| (a) Extraction | (a) Extraction |
| (b) Chemical precipitation | (b) — |
| (c) — | (c) Enzymatic treatment |
| (d) Filtration | (d) Filtration |
| (e) Evaporation | (e) Evaporation |
| (f) Cooking | (f) — |
| (g) Crystallization | (g) Crystallization or granulation (final) |
| (h) Centrifugation (triple) Sugar (sucrose) Syrup (discard) | |

It will be noted that in the enzymatic process of the present invention the operation for producing a dry crystalline or amorphous product which is a single solid phase terminates in the crystallizer or granulator. In the conventional process this stage is constituted by the so called masse cuite (baked paste) which is a mixture of crystals and honey, which mixture must be separated, otherwise both will be lost by fermentation and further reactions. Thus, it can be concluded, with respect to the enzymatic process of the present invention that the carbohydrates and all other solid components found in the initial juice are present in the end product; that there is an absence of secondary carbohydrates, such as gums, colloids, xylose, arabinoses, starch or dextrins, which normally are agents for the high viscosity of juices. To decrease this viscosity the use of surfactants or detergents is required. In the process of the present invention all secondary carbohydrates are transformed in glucose; that there is a reduction of darkening agents and pigments like antocyanins and polyphenols which are unwanted because of their color and taste; that there is a reduction of operational costs and elimination of equipment; that there is an increase of final revenues; and that there are produced natural carbohydrates without partion between solid and liquid phases, which carbohydrates are fully capable of undergoing further developments.

Moreover, by association of the process with the product obtained, a large number of compounds were transformed into glucose, and from an inactive form they were transformed into the most active carbohydrate, D-glucopyranose. Furthermore, these compounds were not destroyed, but reshuffled by the enzymes thereby converting them to a more suitable and usable form. To obtain this, it has been found necessary to use the enzymes in four stages. Otherwise it was not found possible to obtain the end product of the present invention.

The carbohydrates thus obtained are sources of carbon which are useful for the production of other compounds through fermentation, due to the advantages of easy storage, transport and handling.

Tests were undertaken with the pure carbohydrates of the present invention, as well as with these carbohydrates enriched with salts. The results of these tests reveal that high yields were achieved in the production of other compounds, for example yeasts and alcohol, in less time than with carbohydrates produced by conventional processes.

The end product obtained by the current process has a range of applications, such as human nourishment since it exhibits high amounts of sugars (around 92%), mineral salts, essential and non-essential amino-acids and vitamins. The product is also useful as nourishment for animals and for industrial purposes. It is efficiently used as raw material in alcoholic, glutanic and acetic fermentation processes and also in the production of a large range of other products.

With regard especially to alcoholic fermentation, the results obtained using the whole sugar of the present invention for the production of ethanol revealed that the raw material employed was quite superior to conventional sugar as indicated below.

In the production of alcohol, the conventional juice employed contains 55 to 60% of the Total Reducing Sugars whereas the carbohydrates of the enzymatic process of the present invention have 90 to 92% of TRS; the molasses exhibits some non fermentescible carbohydrates whereas all the carbohydrates of the present invention are fermentable; and there is an 82% output without addition of nutrients, reaching 90 to 92% when nutrients are added which represents better results than those of juice fermentation.

What is claimed is:

1. A process for producing carbohydrates from vegetal juice comprising
   (a) extracting said vegetal juice from raw vegetal material,
   (b) filtering said vegetal juice to remove material suspended therein,
   (c) subjecting said vegetal juice resulting from step (b) to an enzymatic reaction consisting of the following four stages in sequence:
      (i) admixing said vegetal juice in the first stage with 3.2.1.4-$\beta$-1,4-glucan glucanhydrolase in an amount of 1.5U and 3.2.1.15-poly-$\alpha$-1,4-galacturonic glucan hydrolase in an amount of 0.9U;
      (ii) admixing said vegetal juice in the second stage with 3.2.1.20-$\alpha$-D-glucoside glucohydrolase in an amount of 0.3U;
      (iii) admixing said vegetal juice in the third stage with 3.2.1.21-$\beta$-D-glucoside glucohydrolase in an amount of 0.3U, 5.3.1.4-L-arabinose-ketol-isomerase in an amount of 0.15U and 5.3.1.5-D-xylose-ketol-isomerase in an amount of 0.15U; and
      (iv) admixing said vegetal juice in the fourth stage with 3.2.1.1-$\alpha$-1,4-glucan-4-glucanhydrolase in an amount of 0.12U and 3.2.1.3-$\alpha$-1,4-glucan glucanhydrolase in an amount of 0.22U, the unit U being the amount of each of the said enzymes required to hydrolyze one mole of starch in 10 minutes,
   (d) filtering the vegetal juice resulting from the enzymatic reaction of step (c) to produce a carbohydrate containing filtrate,
   (e) evaporating under reduced pressure said filtrate to remove water therefrom, and
   (f) crystallizing the product resulting from step (e) thereby producing said carbohydrates in solid form.

2. The process of claim 1 wherein said enzymatic reaction is carried out at a pH ranging from 3.5 to 8, at a temperature ranging from 18° to 67° C. and for a period of time ranging from 20 to 90 minutes.

3. The process of claim 1 wherein subsequent to the enzymatic reaction of step (c) and prior to the filtering the vegetal juice in step (d), the vegetal juice is heated to a temperature ranging from 90° to 100° C. so as to clot any impurities present therein.

4. The process of claim 1 wherein the filtrate is evaporated under reduced pressure in step (e) to remove water therefrom at a temperature of about, but not greater than, 70° C.

5. The process of claim 1 wherein said raw vegetal material is sugar cane, beets, sorghum or any syrup capable of producing crystalline carbohydrates.

* * * * *